(12) United States Patent
Papay et al.

(10) Patent No.: US 6,517,542 B1
(45) Date of Patent: Feb. 11, 2003

(54) BONE ANCHORING SYSTEM

(75) Inventors: Francis A. Papay, Westlake, OH (US); Bryan P. Byerman, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/632,132

(22) Filed: Aug. 3, 2000

Related U.S. Application Data (60) Provisional application No. 60/147,262, filed on Aug. 4, 1999.

(51) Int. Cl.$^7$ .............................................. A61B 17/56
(52) U.S. Cl. ...................................................... 606/73
(58) Field of Search ........................... 606/72, 73, 232

(56) References Cited

U.S. PATENT DOCUMENTS

| | | | |
|---|---|---|---|
| 4,632,100 A | 12/1986 | Somers et al. | |
| 4,950,270 A | 8/1990 | Bowman et al. | |
| 5,019,079 A | 5/1991 | Ross | |
| 5,037,422 A | 8/1991 | Hayhurst et al. | |
| 5,100,417 A | 3/1992 | Cerier et al. | |
| 5,156,616 A | 10/1992 | Meadows et al. | |
| D331,626 S | 12/1992 | Hayhurst et al. | |
| 5,224,946 A | 7/1993 | Hayhurst et al. | |
| 5,234,430 A | 8/1993 | Huebner | |
| 5,236,445 A | 8/1993 | Hayhurst et al. | |
| 5,258,016 A | 11/1993 | DiPoto et al. | |
| 5,300,076 A | 4/1994 | Leriche | |
| 5,372,604 A | 12/1994 | Trott | |
| 5,417,712 A | 5/1995 | Whittaker et al. | |
| 5,472,452 A | 12/1995 | Trott | |
| 5,500,001 A | 3/1996 | Trott | |
| 5,501,683 A | 3/1996 | Trott | |
| 5,522,843 A | 6/1996 | Zang | |
| 5,522,845 A | 6/1996 | Wenstrom, Jr. | |
| 5,571,139 A | 11/1996 | Jenkins, Jr. | |
| 5,584,695 A | 12/1996 | Lal Sachdeva et al. | |
| 5,584,835 A | 12/1996 | Greenfield | |
| 5,591,207 A | 1/1997 | Coleman | |
| 5,607,432 A | 3/1997 | Fucci | |
| 5,628,740 A | 5/1997 | Mullane | |
| 5,690,676 A | 11/1997 | DiPoto et al. | |
| 5,702,397 A | 12/1997 | Goble et al. | |
| 5,720,766 A | 2/1998 | Zang et al. | |
| 5,735,898 A * | 4/1998 | Branemark | 623/16 |
| 5,797,914 A * | 8/1998 | Leibinger | 606/73 |
| 5,849,004 A | 12/1998 | Bramlet | |
| 6,048,343 A * | 4/2000 | Mathis et al. | 606/72 |
| 6,053,916 A | 4/2000 | Moore | |
| 6,123,711 A * | 9/2000 | Winters | 606/73 |
| 6,210,376 B1 | 4/2001 | Grayson | |
| 6,214,012 B1 | 4/2001 | Karpman et al. | |
| 6,368,326 B1 * | 4/2002 | Dakin et al. | 606/103 |

OTHER PUBLICATIONS

"Suture Anchors Aid in Reattaching Soft Tissue to Bone," Johnson & Johnson 1995 Annual Report.
"Arthroscopy Products," Wright Medical Technology, Inc., 1998.
"in–Fast™ Incisionless Transvaginal Cystourethropexy Procedure," Influence, Inc.
"OBL Soft Tissue Anchors," OBL Inc.

(List continued on next page.)

*Primary Examiner*—Eduardo C. Robert
(74) *Attorney, Agent, or Firm*—Tarolli, Sundheim, Covell, Tummino & Szabo L.L.P.

(57) ABSTRACT

A new bone anchoring system comprises a bone screw and a mechanical insert received in a central bore of the bone screw. The bone screw defines a self-tapping, self-boring tip for easy bone insertion as well as through-holes or other openings for receipt of new bone growth. The insert can be replaceably mounted in the bone screw, and a variety of different attachment structures can be defined in the proximal end of the insert for securing to suture thread, tissue or other prosthetic device.

17 Claims, 11 Drawing Sheets

OTHER PUBLICATIONS

"Mainstay® Soft Tissue Anchor," Howmedica Inc., 1997.

F. Alan Barber, M.D., "Strength of Sutures and Suture Anchors, Bioabsorbable Devices,"San Diego Shoulder Arthroscopy Inc., 1997.

F. Alan Barber, M.D., "Strength of Sutures and Suture Anchors, Cancellous Trough," San Diego Shoulder Arthroscopy Inc., 1997.

F. Alan Barber, M.D., "Strength of Sutures and Suture Anchors, 'Mini' Anchors," San Diego Shoulder Arthroscopy Inc., 1997.

"Biologically Quiet™ Screw and Instrumentation," Instrument Makar, Inc., 1998.

"#Quantitative Analysis of Bone Ingrowth into Porous Coated Metal Test Plugs Implanted into Human Cancellous Bone," American Academy of Orthopaedic Surgeons, 1989 Annual Meeting—Scientific Program, modified 1996.

"Rate of Bone Ingrowth of Retrieved Porous–Coated Femoral Hip Prostheses," American Academy of Orthopaedic Surgeons, 1993 Annual Meeting—Scientific Program, modified 1996.

Alexandra K. Schmitt, M.D. et al., "Infection Rate of Coralline Hydroxyapatite in Tibial Plateau, Tibial Pilon and Calcaneal Fractures: A Prospective Study," OTA 1997 Posters—Scientific Basis for Fracture Care.

* cited by examiner

BONE ANCHORING SYSTEM

CROSS-REFERENCE TO RELATED APPLICATION

This case is based on provisional application Ser. No. 60/147,262, filed Aug. 4, 1999, the disclosure of which is incorporated herein by reference and the benefit of which is hereby claimed.

BACKGROUND OF THE INVENTION

1. Field

The present invention relates to an improved bone anchoring system for attaching living tissue or a prosthetic device to bone.

2. Background

U.S. Pat. No. 5,584,695, the disclosure of which is also incorporated herein by reference, describes in FIGS. 7 and 8 a two-part bone anchoring system composed of an anchoring screw and a coupling pin. The anchoring screw is intended to be screwed into a hole previously drilled into the bone. The coupling pin includes a shank shaped to be received in a bore hole in the anchoring screw and, on its proximal end, an eyelet for receiving and holding a suture or prosthetic device. The shank of the coupling pin is made from a material which expands in response to body heat, thereby locking the coupling pin in place in the bore hole of the anchoring screw.

Self-tapping cannulated bone screws are also known. See, for example, U.S. Pat. No. 5,516,616 and U.S. Pat. No. 5,571,139, the disclosures of which are also incorporated herein by reference.

Although the anchoring systems of these patents provide some advantages over earlier technology, there is still a need to provide more secure anchoring, greater flexibility and simpler operation than possible in these systems.

SUMMARY OF THE INVENTION

This and other objects are accomplished by the present invention in accordance with which a new bone anchoring system is provided. This system is composed of a novel self-boring, self-tapping bone screw configured to enhance bone growth and a mechanical insert for mounting in the bone screw. The insert can carry different attaching structures for attachment to suture thread, tissue or other prosthetic device and can be mounted in the bone screw in a variety of different ways. By this means, the inventive anchoring system can be arranged in a variety of different configurations simply and easily and yet still provide secure mounting in all configurations.

Thus, the present invention provides a new bone anchoring system comprising a bone screw defining a self-tapping, self-boring tip and a central bore, and a mechanical insert having a distal end for being received in the central bore and mechanically held by the bone screw, the insert further having a proximal end defining an attachment structure for securing to suture thread, tissue or other prosthetic device, wherein the bone screw includes at least one opening for receipt of new bone growth when the bone screw is screwed in place in a bone.

BRIEF DESCRIPTION OF THE DRAWINGS

The present invention may be more readily understood by reference to the following drawings wherein.

DETAILED DESCRIPTION

The invention comprises a bone anchoring system for attaching sutures, soft tissue, dental prostheses, etc. to a bone and a device to drive the bone anchor into place. The system has the following features:

(1) self, tapping/driving attributes to eliminate the need for predrilling and/or tapping. These anchors may have one or more cutting surfaces;

(2) a hole, slot, hook or similar attribute at the end of the anchor to allow attachment of sutures, tissue, prostheses, etc.;
  (a) a version with integral heads to allow the anchor to be used in specific surgical applications such as orthopedic, plastic and reconstructive, dental, etc.;
  (b) a version with interchangeable heads to allow the anchor to be used in multiple applications by replacing the head, such as orthopedic, plastic and reconstructive, dental, etc.;

(3) a geometry which will allow the anchor to be placed with the end of the bone anchor below the surface of the bone;

(4) surface and other physical modifications of the anchor to promote bone ingrowth which assists in preventing the anchor from backing out;

(5) optional center hole to core the bone in an effort to improve bone ingrowth and increase the ease of implantation;

(6) device to drive the anchor into the bone and a ratchet or similar mechanism on the driver to increase ease of use for the surgeon.

The self-driving and tapping bone anchor eliminates the need to bone drill hole or tapping. A recessed slot or thread holes allows the bone anchor to be utilized with any suture or tissue securing material, or as an attachment site for a prosthetic device, such as dental implant. Surface modifications such as texturing and perforations allow osseous ingrowth for bone ingrowth.

Bone anchors may be utilized in any surgical procedure that requires soft tissue attachment to bone. Bone anchors are currently used in orthopedic surgery, hand surgery, plastic and reconstructive surgery, otolaryngology head and neck surgery, ophthalmologic surgery and dental procedures. Tendons, ligaments, muscles and skin are common soft tissues which may be anchored to bone. Bone anchors may also be utilized to support and/or attach dental prostheses.

Figure 25:
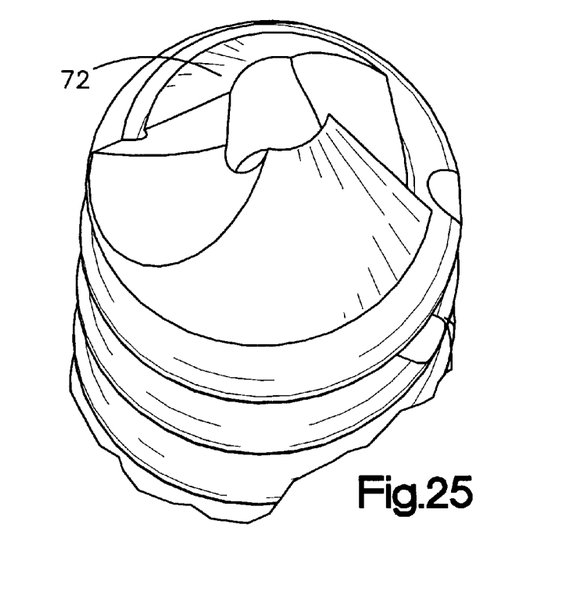
FIG. 25 illustrates the self-boring, self-tapping tip carried on the distal end of the bone screw in the bone anchoring systems of FIGS. 1, 2, 3, 9,10 and 11.

As shown in FIGS. 1, 2, 3, 9, 10 and 11, the inventive bone anchoring system 40 in one embodiment is composed of bone screw 42 and a separate mechanical insert 44, both of which are made from biocompatible materials such as titanium or the like. Bone screw 42 includes a shank 46 defining screw threads 48 for allowing bone screw 42 to be securely mounted in a bone. In addition, bone screw 42 further defines central bore 50, which passes through the distal end of shank 46 so that distal end or tip 72 of the bone screw is annular in configuration. Tip 72 is shaped as illustrated in FIG. 25 to be both self-boring and self-tapping. Accordingly, bone screw 42 can be inserted in place without pre-drilling a pilot hole, although a pilot hole can be provided if desired.

Figure 2:
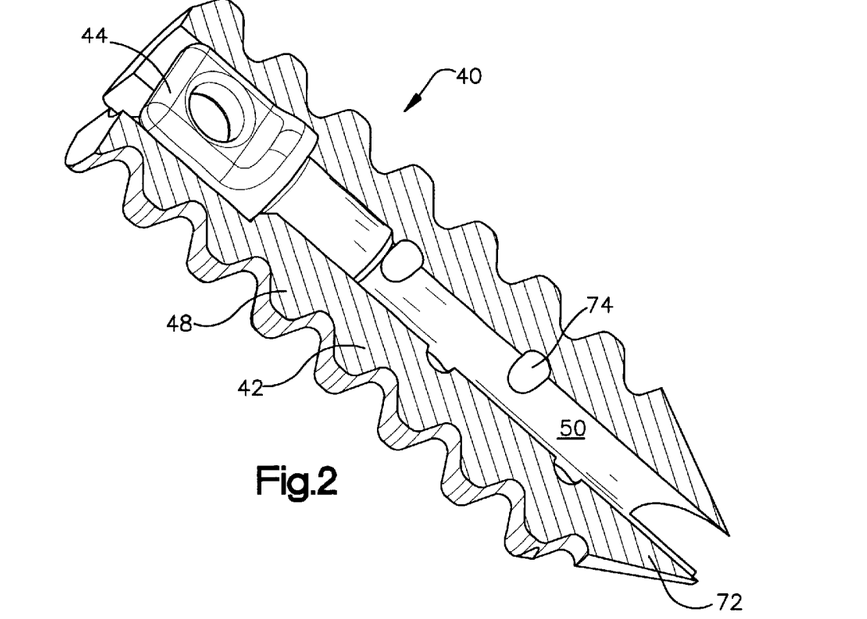
FIGS. 2, 10 and 11 are partial sectional views of the inventive bone anchoring system of FIG. 1.
Figure 3:
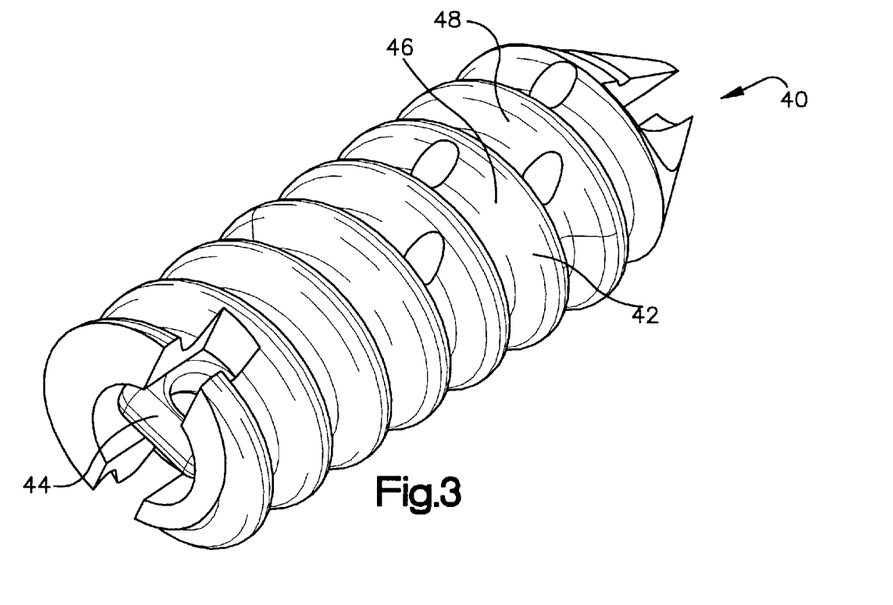
FIGS. 3 and 9 are additional views of the inventive bone anchoring system of FIG. 1.
Figure 10:
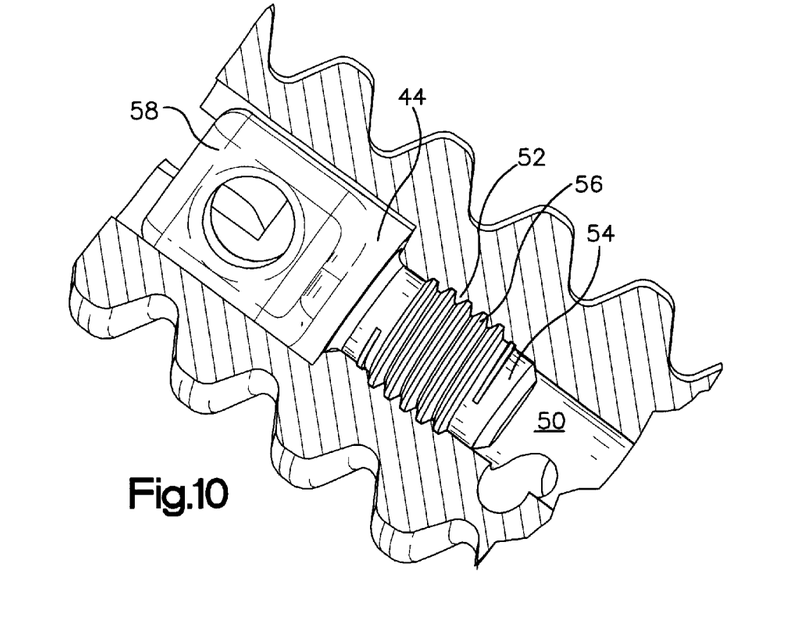
Figure 11:
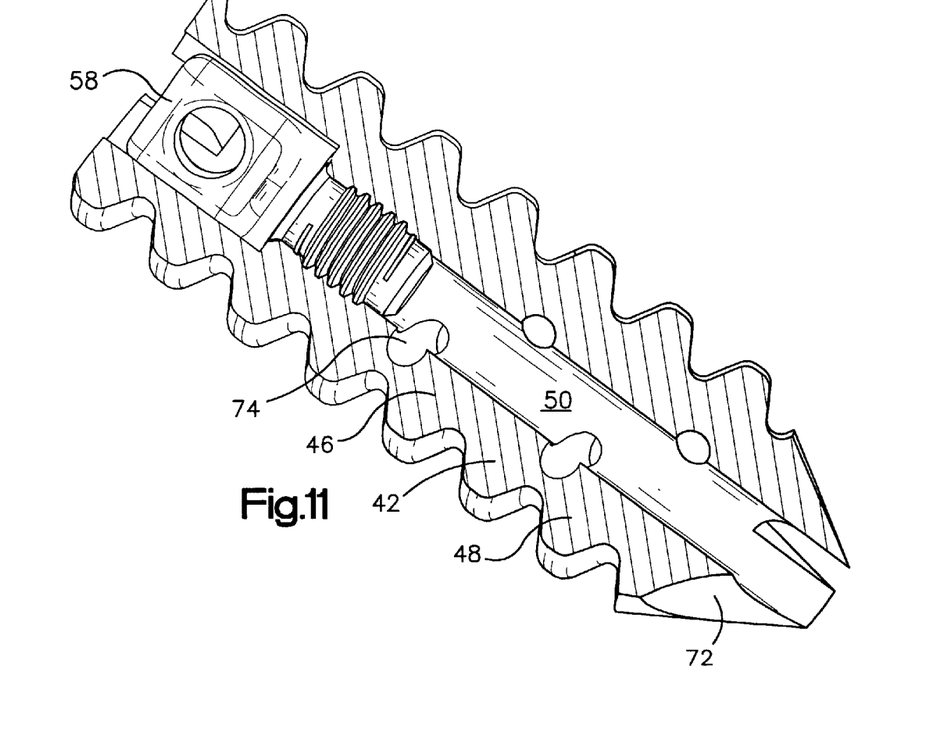

As shown in FIGS. 2, 10 and 11, central bore 50 also extends to the proximal end of the bone screw where it receives mechanical insert 44. The structure of this particular mechanical insert is more clearly shown in FIG. 12. Central bore 50 of bone screw 42 is provided with screw threads 52 for mating with corresponding screw threads 56 carried on the distal end 54 of mechanical insert 44. The proximal end of mechanical insert 44 is provided with an attachment structure 58 for securing suture thread, tissue or other prosthetic device to the inventive bone anchoring system. In the particular embodiment shown, the attachment structure is a closed eyelet 60. By "closed" is meant that the eyelet opening 62 in the eyelet is fully defined throughout a full 360 degrees so that a suture thread fed through this eyelet opening cannot slip out except through its ends. In contrast, an "open" eyelet is one such as illustrated in FIGS. 13 and 14 where a notch or opening is provided in some portion of the eyelet's arc such that eyelet function like a hook.

Figures 12, 13, 14:
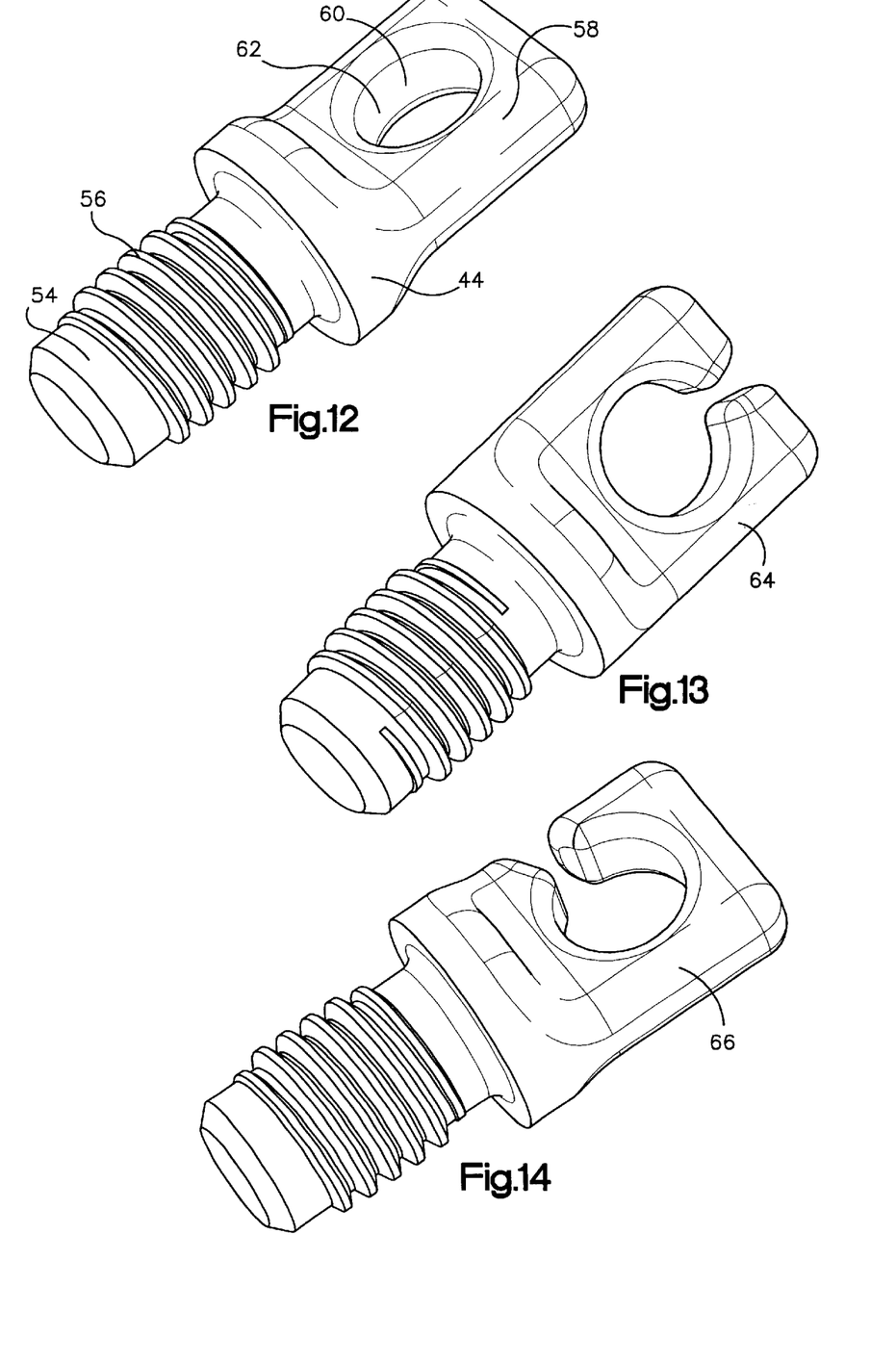
FIGS. 12, 13, 14, 15 and 16 illustrate different mechanical inserts that can be used in the inventive bone anchoring system.
Figure 15:
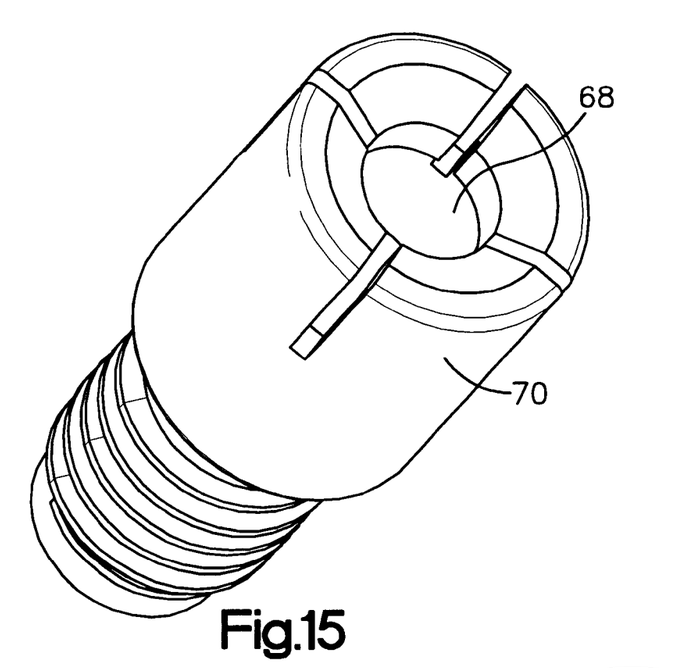
Figure 16:
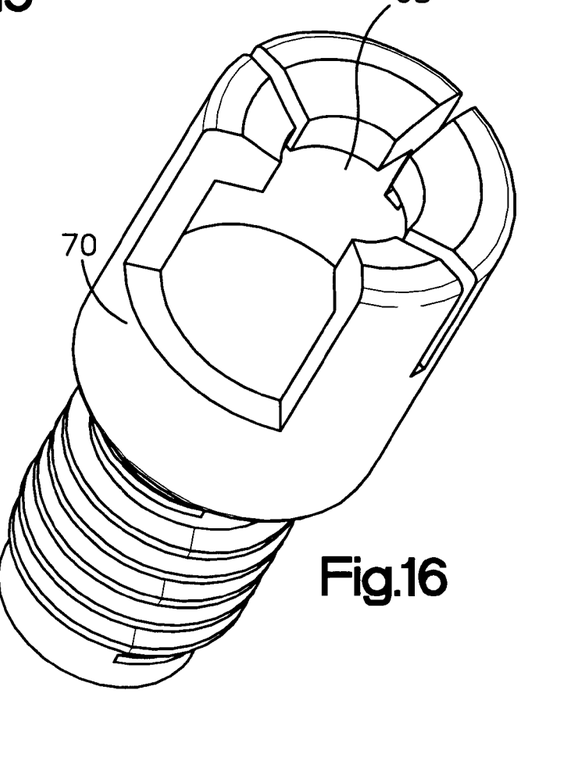

In any event, FIGS. 13 and 14 illustrate that mechanical insert 44 of FIGS. 1, 2, 9 10, 11 and 12 can be replaced by mechanical inserts 64 and 66 of FIGS. 13 and 14, respectively, to provide similar yet different attachment functions. Still another type of attachment function can be provided by the socket type attachment structure 68 as shown in mechanical insert 70 of FIGS. 15 and 16. These figures illustrate that a variety of different attachment functions can be readily and easily provided by the inventive bone anchoring system simply by replacing mechanical insert 44 with another mechanical insert having the desired attachment structure.

Figure 1:
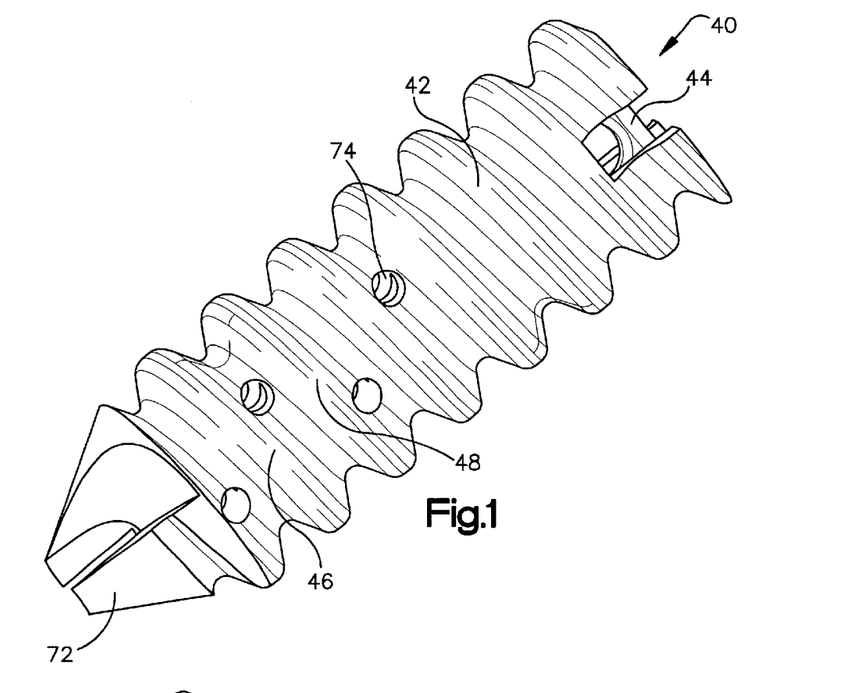
FIG. 1 is an isometric view showing one embodiment of the inventive bone anchoring system in an assembled condition.

As illustrated in FIGS. 1, 2 and 11, shank 46 of bone screw 42 defines multiple through-holes 74, at least some of which preferably communicate with central bore 50. In the particular embodiment shown, these through-holes are arranged at essentially right angles with respect to the central axis of the bone screw. Alternatively, one or more through-holes 74 can be arranged at any other desired angle, although it is preferable that they be arranged in a generally transverse direction. By a "generally transverse" direction is meant that the through-holes are arranged at an angle of at least 45 degrees with respect to the center axis of the bone screw. Through-holes which do not pass through the center axis of the bone screw are "generally transverse when they are arranged at an angle of at least 45 degrees with a line parallel to this central axis. Through-holes which are not straight are "generally transverse" if they are "generally transverse" within the above meanings at their centers.

Through-holes 74 are provided to enhance the osteogenesis process—i.e., to foster bone growth into the interior of the bone screw. To this end, these through-holes (as well as central bore 50) can be coated or provided with a material fostering osteo-inductive or osteo-conductive bone growth, if desired. Examples are bone growth hormones, tricalcium phosphate and the like. Bone growth will occur into the interior of the bone screw, in accordance with the present invention, by growing into through-holes 74. Where through-holes 74 communicate with central bore 50, bone may grow into central bore 50 through these through-holes. Where through-holes 74 do not communicate with central bore 50, bone will nonetheless grow into the interior of bone screw 42 by growing into these through-holes. Also, even where no through-holes 74 are provided, bone will nonetheless grow into the interior of bone screw 42. This is because, as shown in FIG. 25, annular tip 72 is not blocked by any other part of the inventive bone anchoring system (or attached suture thread or prosthetic device) and hence is open to receive new bone growth.

In accordance with the present invention, therefore, bone screw 42 includes at least one opening for receipt of new bone growth when the bone screw is screwed in place in a bone. This enhances the osteogenesis process, thereby locking the bone screw in place over time to provide an exceptionally secure connection. At the same time, however, the inventive bone anchoring system can be put to a variety of different uses simply by choosing a mechanical insert 44 having a different attachment function. And, because mechanical insert 44 is removable, this attaching function can be changed over time as desired. Thus, the inventive anchoring system combines highly flexibility in terms of different possible uses with superior performance in terms of anchoring strength.

Figure 4:
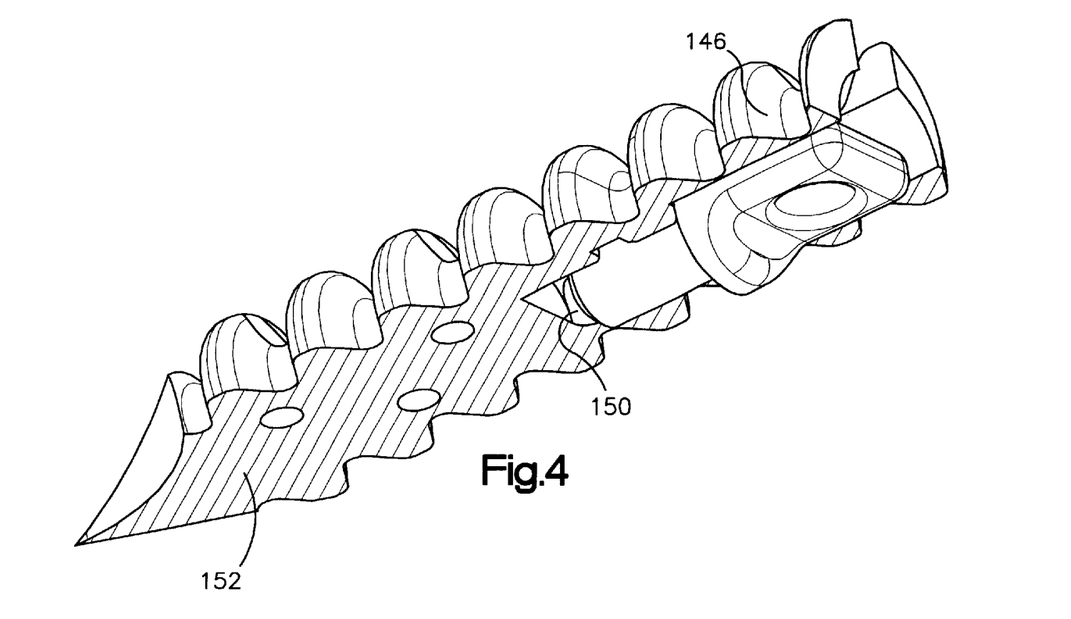
FIG. 4 is a sectional view similar to FIG. 2 showing another embodiment of the invention in which the distal end of the bone screw of the inventive bone anchoring system is essentially solid.

A second embodiment of the inventive bone anchoring system is illustrated in FIG. 4. In this embodiment, central bore 150 in bone screw 142 terminates in the proximal end 146 of the bone screw. Accordingly, the distal end 152 of the bone screw, except for through-holes 174, is essentially solid.

Figure 17:
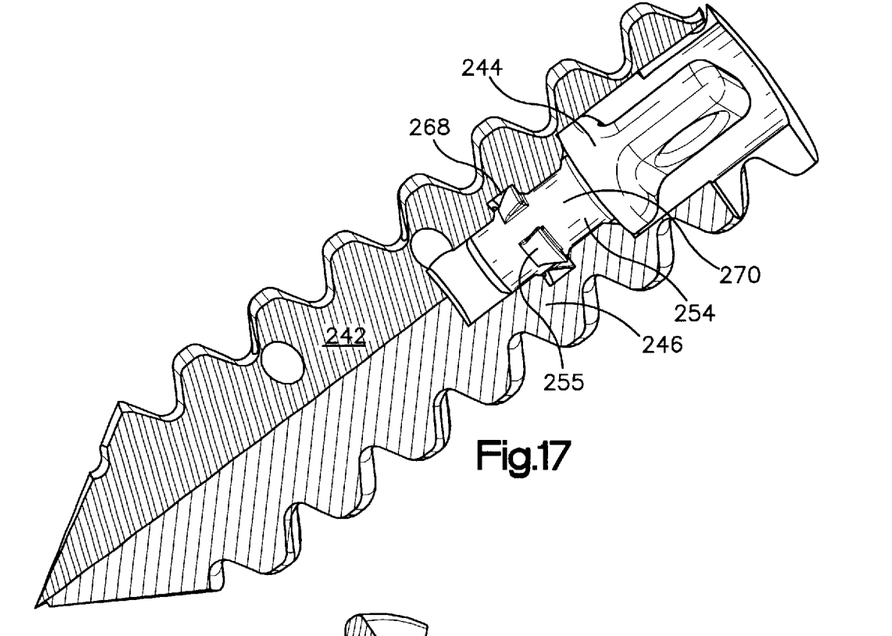
FIGS. 17, 18 and 19 are sectional views illustrating still another embodiment of the inventive bone anchoring system similar to the system of FIG. 4.
Figures 18, 19:
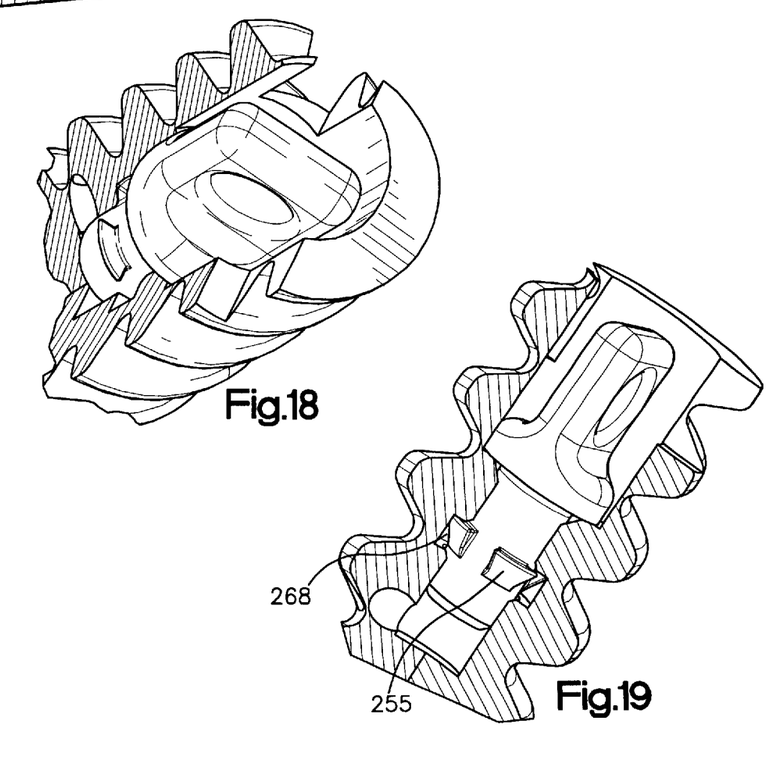
Figures 20, 21:
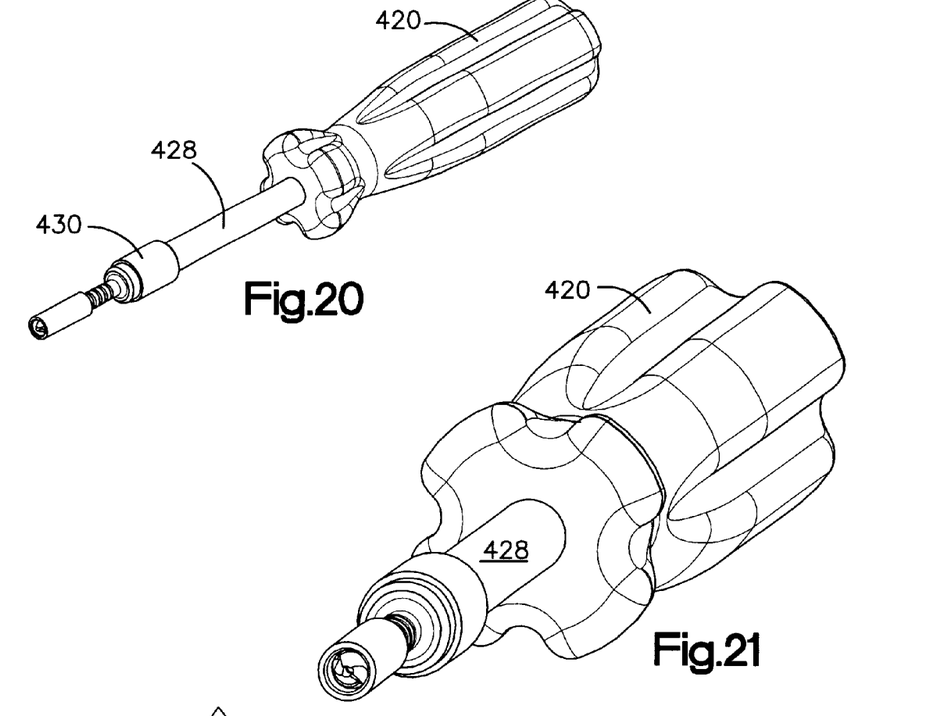
Figure 22:
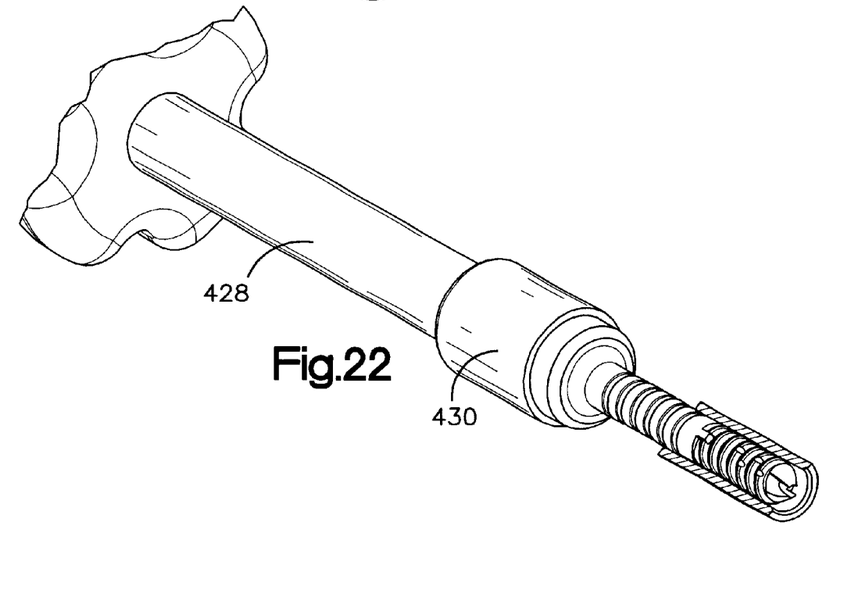

FIGS. 17, 18 and 19 illustrate a third embodiment of the inventive bone anchoring system. This embodiment is essentially the same as the embodiment of FIG. 4, except that distal end 254 of mechanical insert 244 is snap-fit into the proximal end 246 of bone screw 242. In the particular embodiment shown, ridges 255 carried on the distal end of the mechanical insert are received in annular detent 268 defined in the proximal end 270 of bone screw 242. This structure allows mechanical insert 244 to rotate freely about the central axis of the bone screw, as may be desired in some applications.

Figure 5:
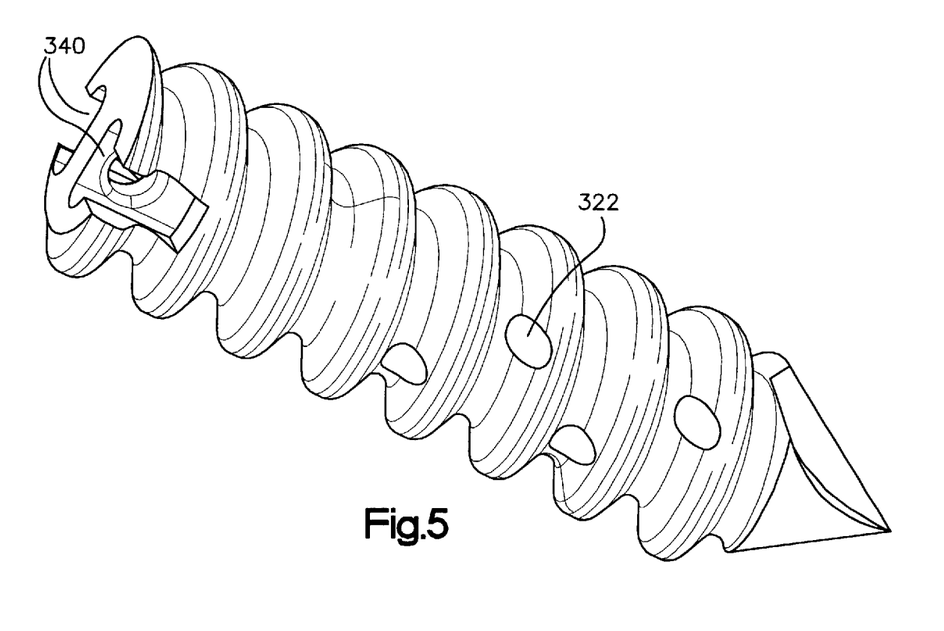
FIGS. 5 and 7 illustrate additional embodiments of the present invention in which the bone screw and insert of the inventive bone anchoring system are made from a single, integral piece of material.
Figures 6, 7:
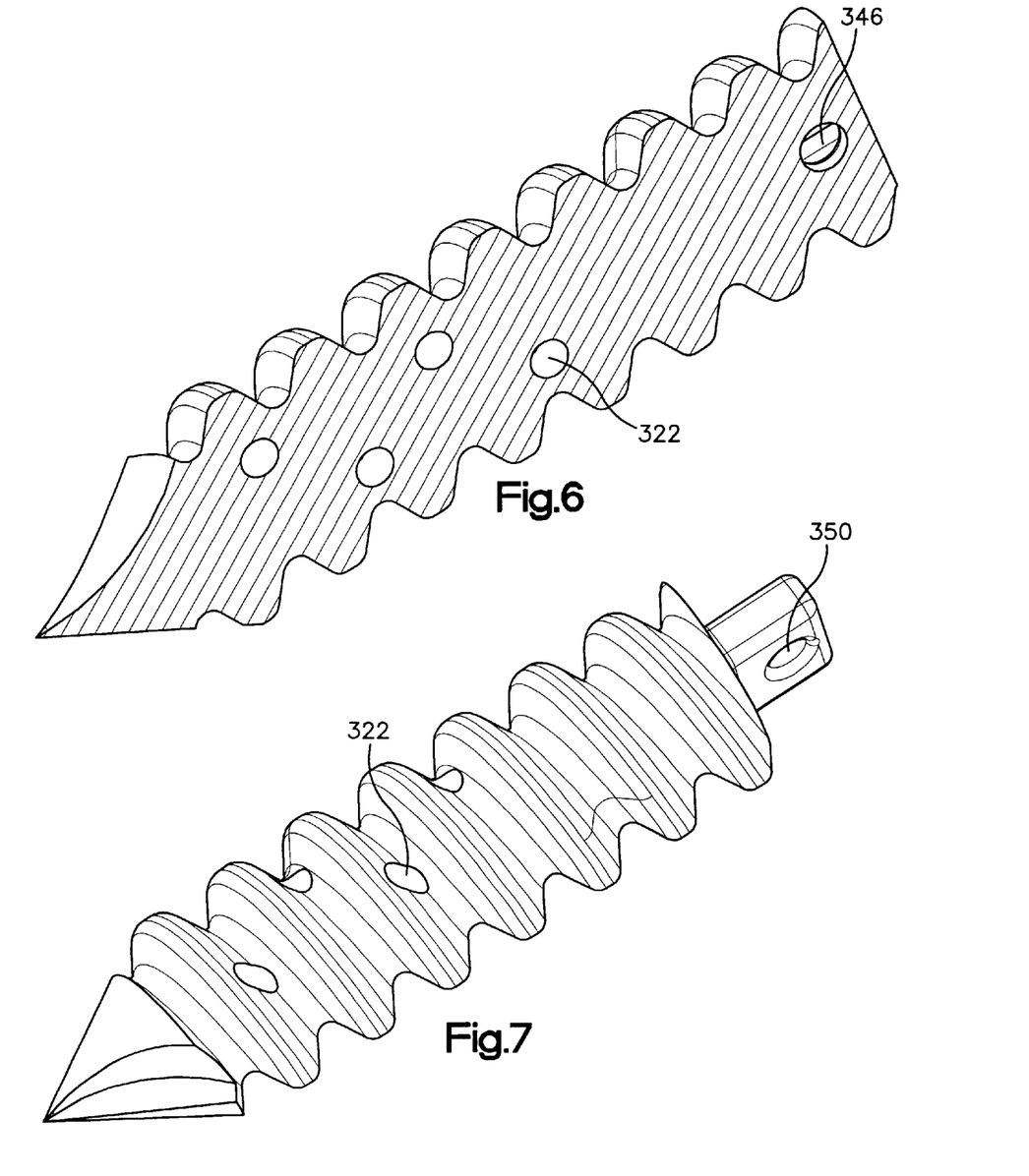
FIG. 6 is a sectional view of the bone anchoring system of FIG. 5.
Figure 8:
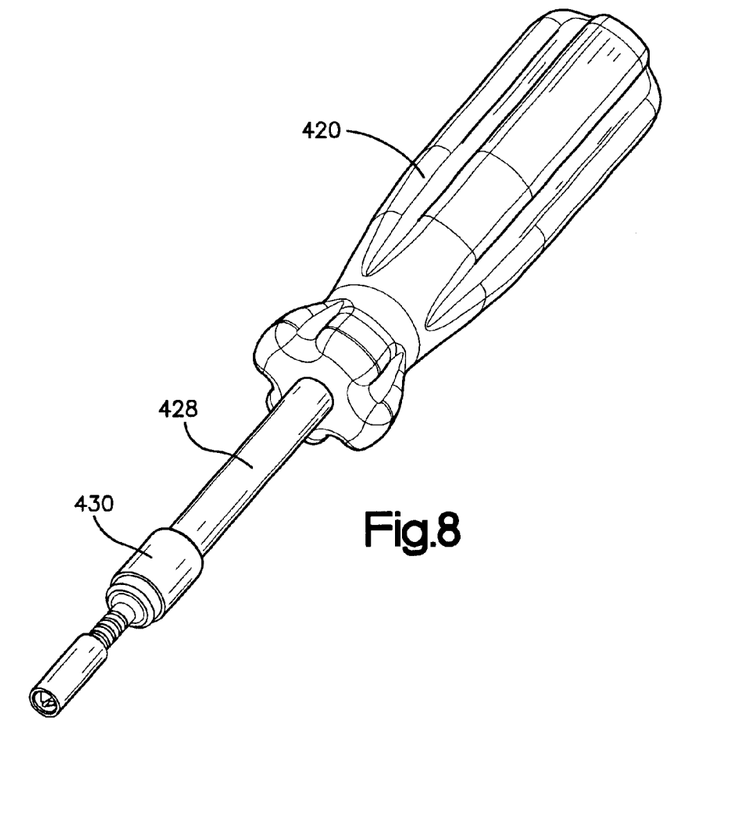
FIGS. 8, 20, 21, 22, 23 and 24 illustrate a drive mechanism useful for inserting the bone screw of the inventive anchoring system in place in a bone.
Figure 9:
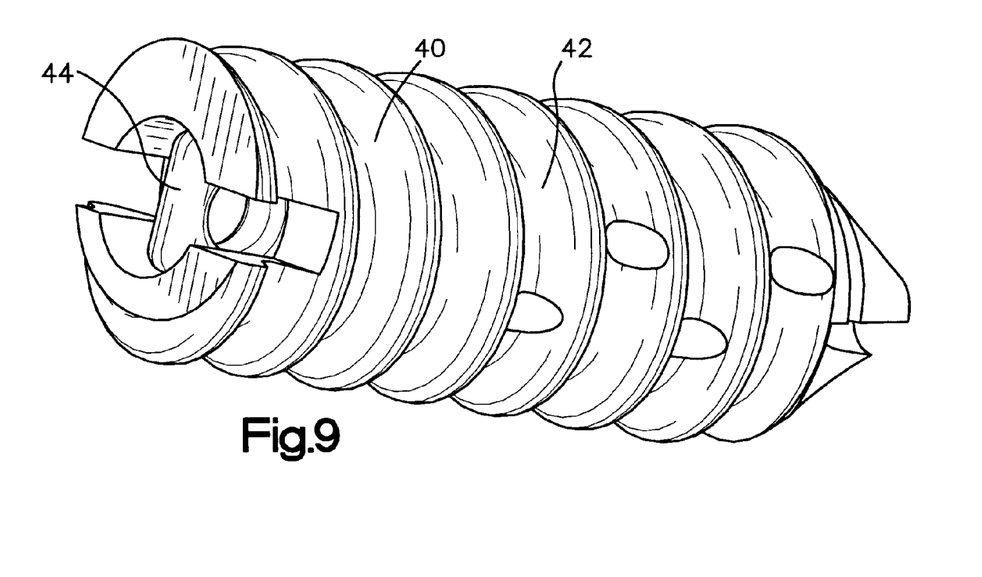

FIGS. 5, 6 and 7 illustrate still additional embodiments of the inventive bone anchoring system in which the bone screw and mechanical insert are formed from a unitary, single piece of material. In these embodiments, a central bore has been eliminated whereby the inventive bone anchoring system is essentially solid. However, as in the embodiments of FIGS. 4, 17, 18 and 19, the distal end of the bone screw in these embodiments is also provided with through-holes 322 for fostering bone growth into the interior of the bone screw. In the embodiment of FIGS. 5 and 6, the proximal end of the bone screw is provided with a drive structure comprising detents 340 for mating engagement with corresponding prongs carried on the head of a driver used for driving the bone screw in place. As shown in FIG. 6, a hole 346 is also provided in the distal end of the bone screw between these detents for receipt of a suture thread, tissue or other prosthetic device. In the embodiment of FIG. 7, the proximal end of the bone screw defines an eyelet 350 having essentially the same structure as closed eyelet 60 of mechanical insert 44 of FIGS. 1, 2, 9 10, 11 and 12.

FIGS. 8, 20, 21, 22, 23 and 24 illustrate a driver that can be used to drive the bone screw of the inventive bone anchoring system in place. This driver includes a handle 420, a drive shaft 428 mounted on the handle and a chuck 430 mounted on the drive shaft. Chuck 430 is adapted to receive and hold a variety of different, interchangeable drive heads so that bone screws of different sizes and having different drive structures can be accommodated by the same drive tool.

The particular drive head 444 illustrated in these figures is composed of a support shaft 446 having essentially the same diameter as the bone screw to be driven in place and support sleeve 448. The outer cylindrical surface of support shaft 446 defines a series of axially-spaced annular detents 450, while the drive structure on the distal end of support shaft 446 includes projections 452 for mating engagement with corresponding detents on the proximal end of bone screw 442 to be driven.

The proximal end of support sleeve 448 carries an annular projection 460 for receipt in annular detents 450 of support shaft 446. In addition, support sleeve 448 is flexible enough so that it can move axially in response to moderate force applied by hand, with annular projection 460 being received by different annular detents 450 in response to this movement.

Figures 23, 24:
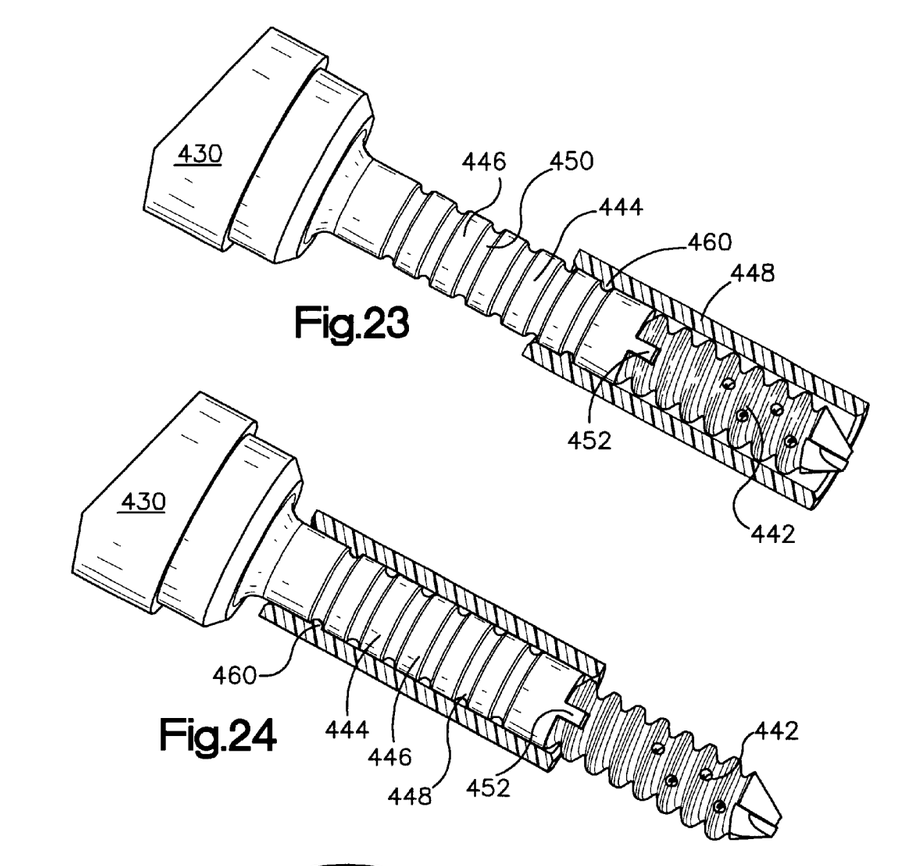

As illustrated in FIGS. 23, this structure allows support shaft 446 to carry and guide bone screw 442 to a desired position before being inserted into a bone. As shown in FIG. 24, this structure also allows automatic withdrawal of bone screw 442 from drive head 444 as the bone screw is screwed into place. This automatic withdrawal occurs as a result of bone at the lip of the bone opening created when the bone screw is driven in place abutting the distal end 468 of support sleeve 448, thereby driving this support sleeve rearwardly as bone screw 442 is driven in place.

Although only a few embodiments of the present invention have been described above, it should be appreciated that many modifications can be made without departing from the spirit and scope of the invention. All such modifications are intended to be included within the scope of the present invention, which is to be limited only by the following claims.

We claim:
1. An apparatus for implantation into a bone and for attaching suture thread, tissue, or a prosthetic device to the bone, said apparatus comprising:
    a first portion having oppositely disposed first and second ends and external screw threads extending between said first and second ends, said first end having a self-tapping tip for cutting into solid non-drilled bone upon rotation of said first portion;
    said first portion including at least one opening for, when implanted, receiving new bone growth; and
    a second portion having oppositely disposed proximal and distal ends, said distal end being connected with said second end of said first portion, said proximal end including structure for attaching at least one of suture thread, tissue, and a prosthetic device;
    said at least one opening in said first portion comprising a central bore extending between said first and second ends, said central bore being open at said first end.

2. The apparatus of claim 1 wherein said first portion comprises an anchor and said second portion comprises an insert.

3. The apparatus of claim 2 wherein said insert threadedly engages said anchor to fixedly connect said insert to said anchor.

4. The apparatus of claim 1 wherein said second portion is received in said central bore at said second end of said first portion.

5. The apparatus of claim 1 wherein said at least opening in said first portion further comprises a plurality of through-holes for, when said first portion is implanted, receiving new bone growth.

6. The apparatus of claim 5 wherein said plurality of through-holes extend radially through said first portion and are in fluid communication with said central bore.

7. The apparatus of claim 1 wherein said at least one opening in said first portion comprises a plurality of radially extending through-holes.

8. An apparatus for implantation into a bone and for attaching suture thread, tissue, or a prosthetic device to the bone, said apparatus comprising:
    a first portion having oppositely disposed first and second ends and external screw threads extending between said first and second ends, said first end having a self-tapping tip for cutting into solid non-drilled bone upon rotation of said first portion;
    said first portion including at least two openings for, when implanted, receiving new bone growth; and
    a second portion having oppositely disposed proximal and distal ends, said distal end being connected with said second end of said first portion, said proximal end including structure for attaching at least one of suture thread, tissue, and a prosthetic device;
    said at least two openings in said first portion comprising a central bore extending between said first and second ends and at least one radially extending through-hole, said central bore being open at said first end.

9. The apparatus of claim 8 wherein said first portion threadedly engages said second portion to fixedly connect said first and second portions.

10. The apparatus of claim 8 wherein said at least one radially extending through-hole comprises a plurality of through-holes in fluid communication with said central bore.

11. The apparatus of claim 8 wherein said at least two openings in said first portion comprise a plurality of radially extending through-holes.

12. An apparatus for implantation into a solid bone and for attaching suture thread, tissue, or a prosthetic device to the bone, said apparatus comprising:

- a first portion having an axis and oppositely disposed first and second ends, said first portion including means for cutting into solid non-drilled bone upon rotation of said first portion and for axially moving said first portion into the solid non-drilled bone upon rotation of said first portion;
- said first portion including at least one opening for, when implanted, receiving new bone growth; and
- a second portion having oppositely disposed proximal and distal ends, said distal end being connected with said second end of said first portion, said proximal end including structure for attaching at least one of suture thread, tissue, and a prosthetic device;
- said at least one opening in said first portion comprising a central bore extending between said first and second ends, said central bore being open at said first end.

13. The apparatus of claim 12 wherein said means for cutting into bone and for axially moving said first portion comprises external screw threads on said first portion and a self-tapping tip for cutting into the solid non-drilled bone.

14. The apparatus of claim 12 wherein said first portion threadedly engages said second portion to fixedly connect said first and second portions.

15. The apparatus of claim 12 wherein said at least opening in said first portion further comprises a plurality of through-holes for, when said first portion is implanted, receiving new bone growth.

16. The apparatus of claim 15 wherein said plurality of through-holes extend radially through said first portion and are in fluid communication with said central bore.

17. The apparatus of claim 12 wherein said at least one opening in said first portion comprises a plurality of radially extending through-holes.

\* \* \* \* \*